United States Patent [19]

Frehel et al.

[11] 4,172,134
[45] Oct. 23, 1979

[54] BENZO [b]THIENOPYRIDINES, PROCESS FOR THEIR PREPARATION AND THERAPEUTIC COMPOSITIONS CONTAINING SAME

[75] Inventors: Daniel Fréhel; Jean-Pierre Maffrand, both of Toulouse, France

[73] Assignee: Parcor, Paris, France

[21] Appl. No.: 908,856

[22] Filed: May 23, 1978

[30] Foreign Application Priority Data

Jun. 2, 1977 [FR] France ............................... 77 16878

[51] Int. Cl.² ................... C07D 521/00; A61K 31/44
[52] U.S. Cl. ...................................... 424/256; 546/80
[58] Field of Search ................. 260/294.8 B; 424/256; 546/80

[56] References Cited

U.S. PATENT DOCUMENTS 3,704,237  11/1972  Suh .................. 260/294.8 B

*Primary Examiner*—Alan L. Rotman
*Attorney, Agent, or Firm*—Young & Thompson

[57] ABSTRACT

This invention relates to compounds having the formula:

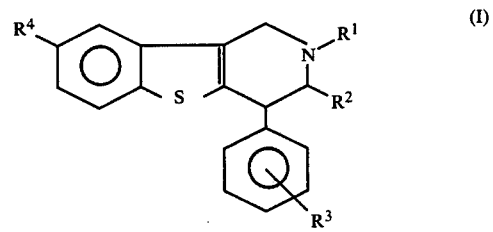

in which:
R¹ represents hydrogen or a lower alkyl group; an aralkyl group optionally substituted on the aromatic nucleus with at least a halogen atom or a hydroxy, nitro, amino, cyano, carboxy, carboxamido, alkoxycarbonyl, lower alkyl, lower alkoxy or trifluoromethyl group; a nicotinyl group; an isonicotinyl group; a picolyl group; a furfuryl group; a 5-methyl-furfuryl group; a 2- or 3-thenyl group; a 5-methyl-2- or 3-thenyl group; or a 5-chloro-2-thenyl group;
R² represents hydrogen or a lower alkyl radical; and
R³ and R⁴ represent each hydrogen, a halogen atom or a hydroxy, lower alkyl or lower alkoxy group,
and their addition salts with inorganic or organic acids.

Said new compounds have typically a therapeutically useful sedative and blood-platelet aggregation inhibiting activity.

5 Claims, No Drawings

BENZO[b]THIENOPYRIDINES, PROCESS FOR THEIR PREPARATION AND THERAPEUTIC COMPOSITIONS CONTAINING SAME

This invention relates to new benzo[b]thienopyridine derivatives, to a process for their preparation and to their applications in human and veterinary medicine.

The derivatives of this invention have the formula:

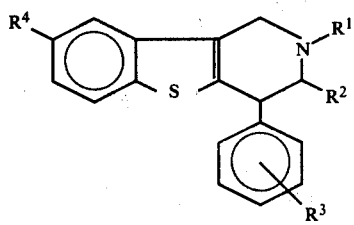

in which:
$R^1$ represents hydrogen or a lower alkyl group; an aralkyl group optionally substituted on the aromatic nucleus with at least a halogen atom or a hydroxy, nitro, amino, cyano, carboxy, carboxamido, alkoxycarbonyl, lower alkyl, lower alkoxy or trifluoromethyl group; a nicotinyl group; an isonicotinyl group; a picolyl group; a furfuryl group; a 5-methyl-furfuryl group; a 2- or 3-thenyl group; a 5-methyl-2- or 3-thenyl group or a 5-chloro-2-thenyl group;

$R^2$ represents hydrogen or a lower alkyl radical; and $R^3$ and $R^4$ represent each hydrogen, a halogen atom or a hydroxy, lower alkyl or lower alkoxy group.

By "lower alkyl" or "lower alkoxy" are meant groups having 1-6 carbon atoms.

The invention includes also within its scope the addition salts of the derivatives of the formula (I) with inorganic or organic acids.

This invention relates also to a process for the preparation of compounds of the formula (I), comprising cyclizing compounds of the formula (II)

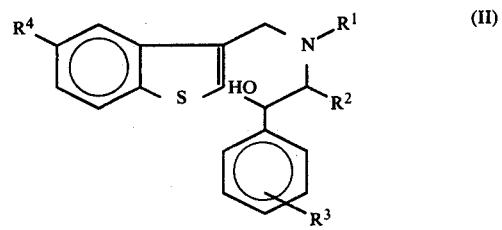

in which $R^1$, $R^2$, $R^3$ and $R^4$ are as defined for formula (I), by heating in polyphosphoric acid, at temperatures between 60° and 80° C.

The cyclization is preferably effected in the presence of an inert gas, typically nitrogen.

The compounds (II) used as intermediates are new compounds which may be prepared by conventional methods. For example, compounds of the formula (II) may be obtained in the following manner:

A 1-phenyl-ethanolamine of the formula (III) given below, in which $R^2$ and $R^3$ have the above-defined meanings, is reacted either with a 3-formyl-benzo[b]thiophene with subsequent reduction, or with a 3-halomethyl-benzo[b]thiophene, to give the compound having the formula (IIa) given below, which is then optionally condensed with a halide of the formula $R^1X$ in which $R^1$ has the aforedefined meaning and X is a halogen (chlorine, bromine or iodine) atom, when it is desired that $R^1$ be other than a hydrogen atom.

The reaction scheme is as follows:

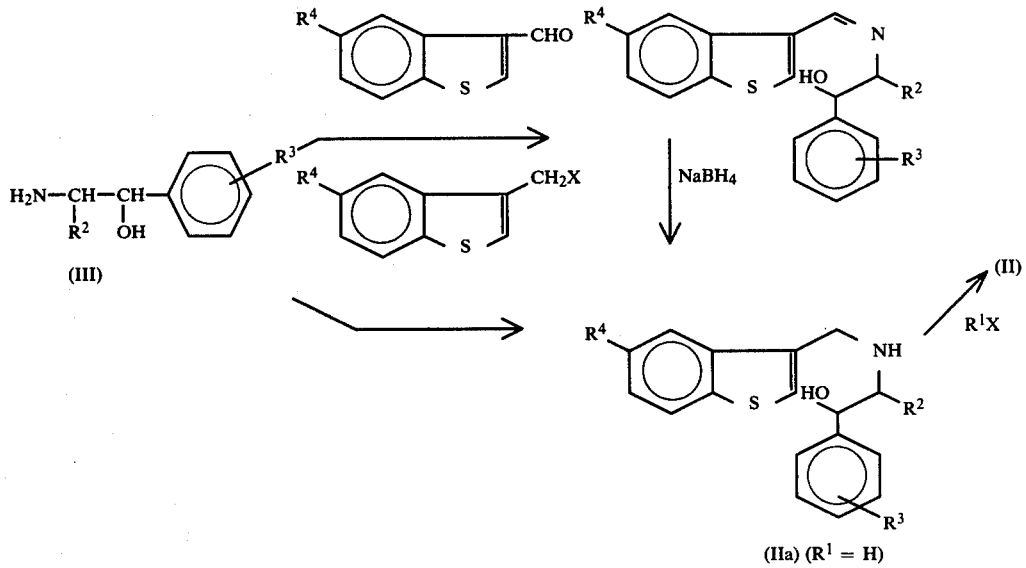

The compounds of the formula (I) in which $R^1$ is other than hydrogen may also be obtained by condensing the corresponding compounds of the formula (I) in which $R^1$ is hydrogen with a compound having the formula $R^1X$ in which X is a halogen atom. The reaction is normally effected within an inert solvent such as ethanol or dimethylformamide, in the presence of a base such as an alkali metal carbonate, potassium carbonate, for example. When X is chlorine or bromine, a catalytic amount of an inorganic iodide such as potassium iodide is advantageously added.

The 2- or 3-halomethyl-benzo[b]thiophenes may be prepared according to the methods disclosed by: S.

AVAKIAN, J. MOSS & G. J. MARTIN, J. Amer. Chem. Soc., 1948, 70, 3075; N. B. CHAPMAN, K. CLARKE, B. GORE & S. N. SAWHNEY, J. Chem. Soc., (C), 1968, 514; N. B. CHAPMAN, K. CLARKE & B. IDDON, J. Chem. Soc., (C), 1965, 774. The 2- and 3-formyl-benzo[b]thiophenes may be prepared according to the methods disclosed by: D. A. SHIRLEY & M. J. DANZIG, J. Amer. Chem. Soc., 1952, 74, 2935; K. CLARKE, C. G. HUGHES, A. J. HUMPHRIES & R. M. SCROWSTON, J. Chem. Soc. (C), 1970, 1013; M. S. EL SHANTA & R. M. SCROWSTON, J. Chem. Soc. (C), 1967, 2085; E. CAMPAIGNE & E. S. NEISS, J. Het. Chem., 1966, 3, 46.

The starting materials of the formula (III) are commercially available or are described in the literature.

The addition salts with inorganic acids (e.g., hydrochloric acid, sulfuric acid, etc.) or organic acids (e.g. methane sulfonic acid, maleic acid, tartaric acid, citric acid, etc.) are prepared according to the usual conventional methods.

The following non-limiting Examples illustrate the invention.

EXAMPLE 1

8-Chloro-3-methyl-4-phenyl-1,2,3,4-tetrahydro-benzo(b)-thieno[3,2-c]pyridine ($R^1=R^3=H$; $R^2=CH_3$; $R^4=Cl$)

(a) Preparation of the amino-alcohol of the formula (II)

A mixture of 3-bromomethyl-5-chloro-benzo(b)thiophene (40 g; 0.153 mole), norephedrine hydrochlorine (28.7 g; 0.153 mole), dry potassium carbonate (42 g; 0.306 mole) and dimethylformamide (400 ml) is heated at 70° C. for 14 hours, under a nitrogen atmosphere. The inorganic salts are filtered off and the solvent is evaporated to dryness under high vacuum. The residual oil is taken up into methylene chloride. The organic extracts are washed with water, dried over dry sodium sulfate and filtered through a silica bed. Evaporation leaves crystals which are recrystallized from cyclohexane: off-white crystals, M.p.=83° C. Yield: 71%.

(b) Cyclization of the amino-alcohol

A mechanically stirred mixture of the above amino-alcohol (16.7 g; 0.05 mole) in commercial polyphosphoric acid (55 g) is heated at 70° C. during 1.5 hours. After cooling, the reaction medium is poured over ice, made basic with concentrated aqueous ammonia and extracted with methylene chloride. The organic extracts are dried over sodium sulfate, filtered through a silica bed and evaporated to dryness.

The resulting crystals are recrystallized from isopropanolmethanol: white crystals, M.p.=174° C.; Yield: 97%.

EXAMPLE 2

3-Methyl-4-phenyl-1,2,3,4-tetrahydro-benzo(b)-thieno[3,2-c]-pyridine ($R^1=R^3=R^4=H$; $R^2=CH_3$)

(a) Preparation of the amino-alcohol of the formula (II)

Said preparation is effected from 3-chloromethyl-benzo(b)-thiophene and norephedrine according to the procedure of Example 1 (part a). Base: white crystals; M.p.=104° C. (cyclohexane). Yield: 67%.

(b) Cyclization of the amino-alcohol

The cyclization is effected according to the procedure of Example 1(b). Base: pinkish-white crystals; M.p.=164° C. (isopropanol). Yield: 72.5%.

EXAMPLE 3

8-Chloro-1-phenyl-1,2,3,4-tetrahydro-benzo(b)-thieno[3,2-c]-pyridine ($R^1=R^2=R^3=H$; $R^4=Cl$)

(a) Preparation of the amino-alcohol of the formula (II)

Said preparation is effected from 3-bromomethyl-5-chlorobenzo(b)thiophene and 2-amino-1-phenyl-ethanol, according to the procedure of Example 1(a). Base: off-white crystals, M.p.=95° C. (cyclohexane). Yield: 40%.

(b) Cyclization of the amino-alcohol

The cyclization is effected according to the procedure of Example 1(b). Methanesulfonate: white crystals; M.p.=234° C. (ethanol); Yield: 77%.

EXAMPLE 4

4-Phenyl-1,2,3,4-tetrahydro-benzo(b)thieno[3,2-c]pyridine ($R^1=R^2=R^3R^4=H$)

(a) Preparation of the aminoalcohol of the formula (II)

Said preparation is effected from 3-chloromethyl-benzo(b)-thiophene and 2-amino-1-phenyl-ethanol, according to the procedure of Example 1(a). Base: white crystals; M.p.=108° C. (cyclohexane); yield: 34%.

(b) Cyclization of the amino-alcohol

The cyclization is effected according to the procedure of Example 1(b). Methanesulfonate: beige crystals; M.p.=215° C. (ethanol); Yield: 69%.

EXAMPLE 5

8-Chloro-2,3-dimethyl-4-phenyl-1,2,3,4-tetrahydro-benzo(b)-thieno[3,2-c]pyridine ($R^1=R^2=$methyl; $R^3=H$; $R^4=Cl$)

The N-methylation of 8-chloro-3-methyl-4-phenyl-1,2,3,4-tetrahydro-benzo(b)thieno[3,2-c]pyridine (Example 1) is effected by condensation with methyl iodide, in ethanol, in the presence of potassium carbonate, or according to the Leuckart reaction (heating in the presence of formalin and formic acid). Hydrochloride: white crystals; M.p.=229° C. (isopropanol). Yield=100% (Leuckart reaction).

EXAMPLE 6

8-Chloro-2-o-chlorobenzyl-3-methyl-4-phenyl-1,2,3,4-tetrahydro-benzo(b)thieno[3,2-c]pyridine ($R^1=$o,chlorobenzyl; $R^2=$methyl; $R^3=H$; $R^4=Cl$).

A mixture of 8-chloro-3-methyl-4-phenyl-1,2,3,4-tetrahydro-benzo(b)thieno[3,2-c]pyridine (Example 1) (6 g; 0.019 mole), o-chlorobenzyl chloride (3.1 g; 0.019 mole) and dry potassium carbonate (2.6 g; 0.019 mole) in dimethylformamide (80 ml) is heated for 12 hours at 70° C. After cooling, the inorganic salts are filtered off and the solvent is evaporated under reduced pressure. The residue is taken up into water and extracted with methylene chloride. The organic extracts are washed with water, dried over sodium sulfate, filtered through a silica bed and evaporated to dryness. The residue is converted to the hydrochloride which is recrystallized from methanol: white crystals, M.p.=175° C. Yield: 55%.

EXAMPLE 7

2-Benzyl-8-chloro-3-methyl-4-phenyl-1,2,3,4-tetrahydro-benzo(b)thieno[3,2-c]pyridine ($R^1$=benzyl; $R^2$=methyl; $R^3$=H; $R^4$=Cl)

Benzyl bromide is condensed with 8-chloro-3-methyl-4-phenyl-1,2,3,4-tetrahydro-benzo(b)thieno[3,2-c]pyridine (Example 1) according to the procedure described in Example 6. Methanesulfonate: white crystals, M.p. >260° C. (acetonitrile) Yield: 63%.

EXAMPLE 8

4-Phenyl-2-p.tolyl-1,2,3,4-tetrahydro-benzo(b)-thieno[3,2-c]-pyridine ($R^1$=p.tolyl; $R^2$=$R^3$=$R^4$=H)

p-Tolyl bromide is condensed with 4-phenyl-1,2,3,4-tetrahydro-benzo(b)thieno[3,2-c]pyridine (Example 4), according to the procedure described in Example 6. Hydrochloride: white crystals; m.p. 200° C. (ethyl acetate-methanol); Yield: 99%.

EXAMPLE 9

3-Methyl-P2-m.methoxybenzyl-4-phenyl-1,2,3,4-tetrahydro-benzo(b)thieno[3,2-c]pyridine ($R^1$=m.methoxybenzyl; $R^3$=$R^4$=H; $R^2$=$CH_3$)

m.Methoxybenzyl bromide is condensed with 3-methyl-4-phenyl-1,2,3,4-tetrahydro-benzo(b)thieno[3,2-c]pyridine (Example 2), according to the procedure described in Example 6. Hydrochloride: white crystals; m.p.=160° C. (acetonitrilemethanol). Yield: 92%.

EXAMPLE 10

8-Chloro-2-(3,4,5-trimethoxy-benzyl)-3-methyl-4-phenyl-1,2,3,4-tetrahydro-benzo(b)thieno[3,2-c]pyridine ($R^1$=3,4,5-trimethoxybenzyl; $R^3$=$R^4$=H; $R^2$=methyl)

3,4,5-Trimethoxy-benzyl chloride is condensed with 8-chloro-3-methyl-4-phenyl-1,2,3,4-tetrahydro-benzo(b)thieno[3,2-c]pyridine (Example 1), according to the process described in Example 6. Base: white crystals, m.p.=172° C. Yield: 78.5%.

EXAMPLE 11

8-Chloro-2-o.nitrobenzyl-4-phenyl-1,2,3,4-tetrahydro-benzo(b)thieno[3,2-c]pyridine ($R^1$=o.nitrobenzyl; $R^2$=$R^3$=H; $R^4$=Cl)

o.Nitrobenzyl chloride is condensed with 8-chloro-4-phenyl-1,2,3,4-tetrahydro-benzo(b)thieno[3,2-c]pyridine (Example 3), according to the procedure described in Example 6. Hydrochloride: yellow crystals, M.p.=150° C. (acetonitrile); Yield: 45%

EXAMPLE 12

2-o.Cyanobenzyl-4-phenyl-1,2,3,4-tetrahydro-benzo(b)-thieno-[3,2-c]pyridine ($R^1$=o.cyanobenzyl; $R^2$=$R^3$=$R^4$=H)

o.Cyanobenzyl bromide is condensed with 4-phenyl-1,2,3,4-tetrahydro-benzo(b)thieno[3,2-c]pyridine (Example 4), according to the procedure of Example 6. Base: off-white crystals; m.p. 143° C.; Yield 69%.

EXAMPLE 13

8-Chloro-3-methyl-2-o.methoxycarbonylbenzyl-4-phenyl-1,2,3,4-tetrahydro-benzo(b)thieno[3,2-c]pyridine ($R^1$=o.methoxycarbonylbenzyl; $R^2$=$CH_3$; $R^3$=H; $R^4$=Cl)

o.Methoxycarbonylbenzyl bromide is condensed with 8-chloro-3-methyl-4-phenyl-1,2,3,4-tetrahydro-benzo(b)thieno[3,2-c]pyridine (Example 1), according to the procedure described in Example 6. Hydrochloride: off-white crystals; m.p. 155° C. (acetonitrile); yield: 86%.

EXAMPLE 14

2-o.Carboxybenzyl-8-chloro-3-methyl-4-phenyl-1,2,3,4-tetrahydro-benzo(b)thieno[3,2-c]pyridine ($R^1$=o.carboxybenzyl; $R^2$=$CH_3$; $R^3$=H; $R^4$=Cl)

This derivative is obtained by basic hydrolysis of the compound described in Example 13. Base: white crystals; m.p.=258° C. (methanol-dimethylformamide); Yield: 100%.

EXAMPLE 15

2-Butyl-8-chloro-3-methyl-4-phenyl-1,2,3,4-tetrahydro-benzo(b)thieno[3,2-c]pyridine ($R^1$=butyl; $R^2$=$CH_3$; $R^3$=H; $R^4$=Cl)

Butyl bromide is condensed with 8-chloro-3-methyl-4-phenyl-1,2,3,4-tetrahydro-benzo(b)thieno[3,2-c]pyridine (Example 1), according to the procedure described in Example 6. Methanesulfonate: white crystals, m.p. 210° C. (acetonitrile); Yield: 58%.

EXAMPLE 16

3-Methyl-2-phenethyl-4-phenyl-1,2,3,4-tetrahydro-benzo(b)-thieno[3,2-c]pyridine ($R^1$=phenethyl; $R^2$=$CH_3$; $R^3$=$R^4$=H)

Phenethyl bromide is condensed with 3-methyl-4-phenyl-1,2,3,4-tetrahydro-benzo(b)thieno[3,2-c]pyridine (Example 2) according to the procedure described in Example 6. Hydrochloride: white crytals, m.p. 210° C. (isopropanol-methanol); Yield : 72%.

EXAMPLE 17

8-Chloro-3-methyl-4-phenyl-2-(3-pyridyl)methyl-1,2,3,4-tetrahydro-benzo(b)thieno[3,2-c]pyridine ($R^1$=(3-pyridyl)methyl; $R^2$=$CH_3$; $R^3$=H; $R^4$=Cl)

3-Chloromethyl-pyridine hydrochloride is condensed with 8-chloro-3-methyl-4-phenyl-1,2,3,4-tetrahydro-benzo(b)thieno[3,2-c]pyridine (Example 1) according to the procedure described in Example 6. Dihydrochloride: pink crystals; m.p.=260° C. (methanoldimethylformamide); Yield: 69%.

EXAMPLE 18

3-Methyl-4-phenyl-2-(2-pyridyl)methyl-1,2,3,4-tetrahydro-benzo(b)thieno[3,2-c]pyridine ($R^1$=(2-pyridyl)methyl ; $R^2$=$CH_3$; $R^3$=$R^4$→H)

2-Chloromethyl-pyridine hydrochloride is condensed with 3-methyl-4-phenyl-1,2,3,4-tetrahydro-benzo(b)-thieno[3,2-c]pyridine (Example 2) according to the procedure described in Example 6. Dihydrochloride: off-white crystals; m.p.=155° C. (ethyl acetatemethanol); Yield: 63%.

EXAMPLE 19

8-Chloro-3-methyl-4-phenyl-2-(4-pyridyl)methyl-1,2,3,4,-tetrahydrobenzo(b)thieno[3,2-c]pyridine ($R^1$=(4-pyridyl)methyl; $R^2$=$CH_3$; $R^3$=H; $R^4$=Cl)

4-Chloromethyl-pymidine hydrochloride is condensed with 8-chloro-3-methyl-4-phenyl-1,2,3,4-tetrahydro-benzo(b)thieno[3,2-c]pyridine, according to the procedure described in Example 6. Dihydrochloride: light brown crystals; m.p.=258° C.; Yield: 41%.

The results of toxicological and pharmacological tests reported below demonstrate the valuable activities of the derivatives of this invention, particularly their blood-platelet aggregation inhibiting activity and their sedative activity.

Thus, this invention includes also within its scope a therapeutic composition having in particular blood-platelet aggregation inhibiting activities and sedative activities, comprising, as active ingredient, a derivative of the formula (I) or a pharmaceutically acceptable acid-addition salt thereof, together with a therapeutically administrable carrier.

I—TOXICOLOGICAL INVESTIGATION

The compounds of this invention benefit from an excellent tolerance and a low toxicity. Thus, the $LD_{50}$/24 hrs/kg of animal, determined in mice according to the method of Miller and Tainter, by the oral route, is in excess of 400 mg for all derivatives.

In addition, the tests effected on acute, chronic, sub-chronic and delayed toxicity in various animals species failed to evidence any local or systemic reaction, any perturbation in the regularly effected biological controls, any anomaly in the microscopic and macroscopic examinations effected in the animals sacrificed and autopsied at the end of the experimentation.

II—PHARMACOLOGICAL INVESTIGATION

1. Blood-platelet aggregation inhibiting activity

Blood is taken from the jugular vein of Wistar rats. From this citrated blood and after centrifugation, is reconstituted a plasma containing 600,000±20,000 blood-platelets per mm3 which will be used in all aggregation determinations.

(a) Determination of A.D.P. induced blood-platelet aggregation 0.4 ml of plasma is placed in a siliconized tube provided with a magnet bar which is also siliconized. The tube is introduced into an aggregometer connected with an apparatus which records optical density variations. When light transmission has attained a stable value, 0.5 ml of a solution containing 10 μM A.D.P. (Adenosine-Di-Phosphate) are introduced into the tube.

Blood-platelet aggregation then produces an increase of light transmission followed by a decrease subsequent to the deaggregation phase.

The maximal optical density variation thus determined characterizes the intensity of the aggregation.

(b) Determination of collagen-induced blood-platelet aggregation

The A.D.P. solution is substituted with a collagen solution (bovine tendon extract).

(c) Results

Different groups of 20 rats each are used, each group being orally administered a test derivative at a dosage of 100 mg/kg. The results obtained in the course of both tests are reported in following Table I which indicates the percent inhibition of bloodplatelet aggregation obtained with respect to the reference group, 3 hours after treatment with the compound of this invention, in the A.D.P. and the collagen tests.

TABLE I

| Treatment | Percent inhibition | |
|---|---|---|
| | A.D.P. | Collagen |
| derivative of Example 1 | 62.1 | 91.4 |
| derivative of Example 2 | 61.7 | 93.8 |
| derivative of Example 3 | 62.9 | 90.5 |
| derivative of Example 4 | 61.5 | 90.8 |
| derivative of Example 5 | 60.8 | 91.2 |
| derivative of Example 6 | 61.2 | 94.4 |
| derivative of Example 7 | 63.0 | 95.1 |
| derivative of Example 8 | 61.4 | 90.6 |
| derivative of Example 9 | 61.8 | 91.2 |
| derivative of Example 10 | 60.2 | 94.5 |
| derivative of Example 11 | 62.5 | 92.7 |
| derivative of Example 12 | 61.3 | 92.2 |
| derivative of Example 13 | 62.1 | 95.0 |
| derivative of Example 14 | 60.6 | 93.8 |
| derivative of Example 15 | 60.1 | 92.6 |
| derivative of Example 16 | 62.7 | 93.2 |
| derivative of Example 17 | 63.5 | 90.4 |
| derivative of Example 18 | 61.3 | 91.7 |
| derivative of Example 19 | 62.4 | 91.9 |

2. Sedative action

The sedative action of the compounds of this invention was investigated according to several methods.

(A) Study of the behavior

This study was effected according to the method of SAMUEL IRWIN (PH.D.; Animal and Clinical Pharmacology Technics in Drug Evaluation). The derivatives of this invention are orally administered to mice at a dosage of 100 mg/kg. The study of the behavior of the animals treated, in the course of the 4 hours following administration, together with the determination of the various physiological parameters, temperature, cardiac rate and respiratory rate, provides evidence of the marked sedative action of the derivatives of this invention.

(B) Action with respect to hypnotic drugs

The test compounds are administered to mice, by the oral route, at a dosage of 100 mg/kg, 30 minutes prior to intraperitoneal injection of a solution of 300 ml chloral in 20 ml physiological saline solution. The number of mice which have fallen asleep, the time required for the mice to fall asleep and the sleeping time are recorded with respect to reference mice which have been administered only the chloral injection. It is found that the derivatives of this invention provide a considerable potentiation of the action of chloral with respect to the duration of the sleep thus induced and to the number of mice which have fallen asleep.

(C) Traction test

This test comprises suspending to a wire, by the forelimbs, mice which have been orally administered 100 mg of the test derivative. The mice are considered as having been submitted to a sedative action when—within a period of time of 30 seconds—they fail to straighten up by at least placing one of their hind limbs on the wire.

The animals are tested prior to the experiment, and those which fail to straighten up within 30 seconds are eliminated. In the course of the tests, it is found that only 10% of the test animals are capable of successfully straightening up.

(D) 4-Plate test (Boissier, Simon & Aron, Europ. J. of Pharmacol. 4, 1968, 145-151)

A mouse, placed in an enclosure containing 4 electrified plates receives, whenever it passes from one plate to another, an electric stimulus which induces helter-skelter flight. After n electric shocks, the mouse does not move any more. It is considered that the degree of sedation obtained is proportional to the number n of electric stimuli received by the treated mouse before standing still in a corner.

It is thus determined that, an oral administration at a dosage of 100 mg/kg, the derivatives of this invention produce an average percent increase of the number n of electric stimuli of the order of 60% after 15 minutes, of 62% after 30 minutes and of 51% after 90 minutes.

The results of the above investigations demonstrate the good tolerance of the derivatives of this invention together with their useful sedative and blood-platelet inhibiting properties which make then valuable in human and veterinary medicine.

For oral administration, the therapeutic composition of this invention may be formulated as tablets, coated tablets, capsules, drops or syrups. For rectal administration, it may also be formulated as suppositories and, for parenteral administration, as injectable solutions.

Each unit dose contains advantageously 0.010–0.500 g active ingredient, the daily dosage regimen varying from 0.010 g to 1.00 g active ingredient, depending on the age of the patient and the condition being treated.

Non-limiting Examples of pharmaceutical formulations of the therapeutic composition of this invention are given below.

1. TABLETS

| Derivative of Example 2 | 0.050 g |
|---|---|

Excipient: corn starch, magnesium stearate, Aerosil, talc, amaranth, tartrazine

2. COATED TABLETS

| Derivative of Example 6 | 0.075 g |
|---|---|

Excipient: talc, corn starch, gum arabic, shellac, sugar, glucose, white wax, Carnauba wax, spermaceti, lactose, orange yellow S, titanium dioxide

3. CAPSULES

| Derivative of Example 9 | 0.100 g |
|---|---|

Excipient: magnesium stearate, corn starch, sucrose.

4. INJECTABLE AMPOULES

| Derivative of Example 14 | 0.050 g |
|---|---|

Excipient: isotonic solution, sufficient to make 5 ml

5. SUPPOSITORIES

| Derivative of Example 18 | 0.100 g |
|---|---|

Excipient: semi-synthetic triglycerides

6. SYRUP

| Derivative of Example 2 | 1.00 g |
|---|---|

Flavoured excipient, sufficient to make 100 ml

The toxicological and pharmacological investigations reported above provide evidence of the good tolerance of the derivatives of this invention together with their sedative and blood-platelet aggregation inhibiting properties.

Thus, the therapeutic composition of this invention may be advantageously administered for preventive or curative purposes in the treatment of diseases inducing a pathological modification of blood-platelet aggregation, such as thrombo-embolic diseases.

It may also be administered as a sedative and a control agent for the nervous system in cases of nervous erethism, neurotony, states of excitation with insomnia, and in cases of mental disorders.

Having now described our invention what we claim as new and desire to secure by Letters Patent of the U.S. is:

1. A compound selected from the compounds having the formula:

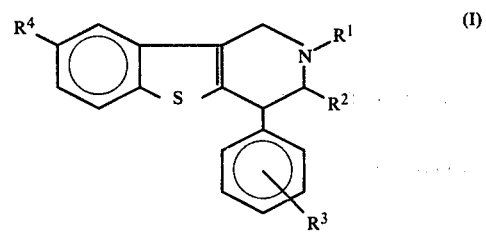

in which:
$R^1$ is selected from hydrogen; $C_{1-6}$ alkyl; phenyl, tolyl, benzyl; benzyl substituted on the ring by a halogen atom, a nitro group, a cyano group, a carboxy group, a methoxycarbonyl group or one to three methoxy groups; phenethyl; (2-pyridyl)-methyl; (3-pyridyl)-methyl and (4-pyridyl)-methyl;
$R^2$ is selected from hydrogen and $C_{1-6}$ alkyl; and
$R^3$ and $R^4$ are independently selected from hydrogen, halogen, hydroxy, $C_{1-6}$ alkyl and $C_{1-6}$ alkoxy;
and the pharmaceutically acceptable acid addition salts of said compounds.

2. Therapeutic composition having a sedative activity comprising an effective amount of an active compound selected from the compounds having the formula:

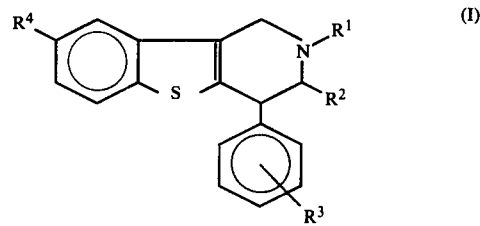

in which:
$R^1$ is selected from hydrogen; $C_{1-6}$ alkyl; phenyl, tolyl, benzyl; benzyl substituted on the ring by a halogen atom, a nitro group, a cyano group, a carboxy group, a methoxycarbonyl group or one to three methoxy groups; phenethyl; (2-pyridyl)-methyl; (3-pyridyl)-methyl and (4-pyridyl)-methyl;
$R^2$ is selected from hydrogen and $C_{1-6}$ alkyl; and
$R^3$ and $R^4$ are independently selected from hydrogen, halogen, hydroxy, $C_{1-6}$ alkyl and $C_{1-6}$ alkoxy;

and the pharmaceutically acceptable acid addition salts of said compounds, together with a therapeutically administrable carrier.

3. Therapeutic composition as claimed in claim 2, in unit dosage form, wherein each unit dose contains 0.010–0.500 g active compound.

4. Therapeutic composition having a blood-platelet aggregation inhibiting activity comprising an effective amount of an active compound selected from the compounds having the formula:

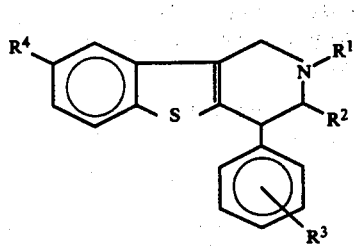

in which:
R[1] is selected from hydrogen; $C_{1-6}$ alkyl; phenyl, tolyl, benzyl; benzyl substituted on the ring by a halogen atom, a nitro group, a cyano group, a carboxy group, a methoxycarbonyl group or one to three methoxy groups; phenethyl; (2-pyridyl)-methyl; (3-pyridyl)-methyl and (4-pyridyl)-methyl;
R[2] is selected from hydrogen and $C_{1-6}$ alkyl; and
R[3] and R[4] are independently selected from hydrogen, halogen, hydroxy, $C_{1-6}$ alkyl and $C_{1-6}$ alkoxy;
and the pharmaceutically acceptable acid addition salts of said compounds, together with a therapeutically administrable carrier.

5. Therapeutic composition as claimed in claim 4, in unit dosage form, wherein each unit dose contains 0.010–0.500 g active compound.

* * * * *